United States Patent
Vitek et al.

(10) Patent No.: US 9,623,266 B2
(45) Date of Patent: Apr. 18, 2017

(54) ESTIMATION OF ALIGNMENT PARAMETERS IN MAGNETIC-RESONANCE-GUIDED ULTRASOUND FOCUSING

(75) Inventors: Shuki Vitek, Haifa (IL); Rita Schmidt, Givataim (IL); Amir Seginer, Tel Aviv (IL)

(73) Assignee: INSIGHTEC LTD., Tiral Carmel (IL)

( * ) Notice: Subject to any disclaimer, the term of this patent is extended or adjusted under 35 U.S.C. 154(b) by 2086 days.

(21) Appl. No.: 12/535,004

(22) Filed: Aug. 4, 2009

(65) Prior Publication Data
US 2011/0034800 A1 Feb. 10, 2011

(51) Int. Cl.
| | |
|---|---|
| A61B 5/055 | (2006.01) |
| A61N 7/02 | (2006.01) |
| G01R 33/48 | (2006.01) |
| A61B 8/00 | (2006.01) |
| A61B 17/00 | (2006.01) |
| A61N 7/00 | (2006.01) |
| A61B 90/00 | (2016.01) |

(52) U.S. Cl.
CPC ............... *A61N 7/02* (2013.01); *A61B 5/055* (2013.01); *A61B 8/587* (2013.01); *G01R 33/4814* (2013.01); *A61B 2017/00725* (2013.01); *A61B 2090/374* (2016.02); *A61B 2090/3954* (2016.02); *A61N 2007/0065* (2013.01); *A61N 2007/0078* (2013.01); *A61N 2007/0095* (2013.01)

(58) Field of Classification Search
CPC .... A61B 2017/00725; A61B 2090/374; A61B 2090/3954; A61B 5/055; A61B 8/587; A61N 2007/0065; A61N 2007/0078; A61N 2007/0095; A61N 7/02; G01R 33/4814
USPC ....... 600/407, 410, 411, 412, 422, 424, 437, 600/459; 378/18, 19, 20, 55, 63; 382/128, 191
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |

(Continued)

FOREIGN PATENT DOCUMENTS

| | | |
|---|---|---|
| DE | 4345308 C2 | 2/2001 |
| DE | 10102317 | 8/2002 |

(Continued)

OTHER PUBLICATIONS

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).

(Continued)

*Primary Examiner* — Ruth S Smith
(74) *Attorney, Agent, or Firm* — Morgan, Lewis & Bockius LLP

(57) ABSTRACT

A magnetic-resonance-guided focused ultrasound system may be calibrated by generating ultrasound foci using ultrasound transducers, establishing coordinates of the foci and of magnetic-resonance trackers associated with the transducers, and determining a geometric relationship between the trackers and the transducers.

19 Claims, 4 Drawing Sheets

(56) References Cited

U.S. PATENT DOCUMENTS

| | | |
|---|---|---|
| 3,992,693 A | 11/1976 | Martin et al. |
| 4,000,493 A | 12/1976 | Spaulding et al. |
| 4,074,564 A | 2/1978 | Anderson |
| 4,206,653 A | 6/1980 | Lemay |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,636,964 A | 1/1987 | Jacobs et al. |
| 4,662,222 A | 5/1987 | Johnson |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,339,282 A * | 8/1994 | Kuhn et al. ................ 367/7 |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,557,438 A * | 9/1996 | Schwartz et al. .......... 359/204.1 |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,810,008 A | 9/1998 | Dekel et al. |
| 5,817,036 A | 10/1998 | Anthony et al. |
| 5,831,739 A * | 11/1998 | Ota ................ 356/401 |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A * | 3/2000 | Beach et al. ................ 601/3 |
| 6,071,239 A | 6/2000 | Cribbs et al. |
| 6,113,558 A | 9/2000 | Rosenschein et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,554,826 B1 | 4/2003 | Deardorff |
| 6,559,644 B2 | 5/2003 | Froundlich et al. |
| 6,566,878 B1 | 5/2003 | Komura et al. |
| 6,582,381 B1 | 6/2003 | Marantz et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,264,592 B2 | 9/2007 | Shehada |

(56) References Cited

U.S. PATENT DOCUMENTS

| | | |
|---|---|---|
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,452,357 B2 | 11/2008 | Vlegele et al. |
| 7,462,488 B2 * | 12/2008 | Madsen et al. ............... 436/8 |
| 7,505,805 B2 | 3/2009 | Kuroda |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2002/0188229 A1 | 12/2002 | Ryaby |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030227 A1 | 2/2004 | Littrup et al. |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0147919 A1 | 7/2004 | Behl et al. |
| 2004/0199068 A1 | 10/2004 | Bucholz et al. |
| 2004/0210134 A1 | 10/2004 | Hynynen et al. |
| 2004/0236253 A1 | 11/2004 | Vortman et al. |
| 2004/0267126 A1 | 12/2004 | Takeuchi |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0203444 A1 | 9/2005 | Schonenberger et al. |
| 2005/0240126 A1 | 10/2005 | Foley et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 * | 3/2006 | Hynynen et al. ............. 600/459 |
| 2006/0058671 A1 * | 3/2006 | Vitek et al. ................. 600/447 |
| 2006/0058678 A1 | 3/2006 | Vitek et al. |
| 2006/0079773 A1 * | 4/2006 | Mourad et al. .............. 600/438 |
| 2006/0106300 A1 | 5/2006 | Seppenwoolde et al. |
| 2006/0173385 A1 | 8/2006 | Lidgren et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2007/0016013 A1 * | 1/2007 | Camus ........................ 600/424 |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0197918 A1 | 8/2007 | Vitek et al. |
| 2007/0219470 A1 | 9/2007 | Talish et al. |
| 2008/0027342 A1 | 1/2008 | Rouw et al. |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0108900 A1 | 5/2008 | Lee et al. |
| 2008/0183077 A1 | 7/2008 | Moreau-Gobard et al. |
| 2008/0228081 A1 | 9/2008 | Becker et al. |
| 2008/0249408 A1 * | 10/2008 | Palmeri et al. .............. 600/438 |
| 2008/0292194 A1 * | 11/2008 | Schmidt et al. ............. 382/217 |
| 2008/0312562 A1 | 12/2008 | Routh et al. |
| 2009/0088623 A1 | 4/2009 | Vortman et al. |
| 2009/0096450 A1 | 4/2009 | Roland |
| 2010/0056962 A1 | 3/2010 | Vortman et al. |

FOREIGN PATENT DOCUMENTS

| | | |
|---|---|---|
| EP | 1132054 | 9/2001 |
| EP | 1582886 | 10/2005 |
| EP | 151073 | 11/2005 |
| EP | 1774920 A1 | 4/2007 |
| EP | 1790384 | 5/2007 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | WO-0031614 | 6/2000 |
| WO | WO-0031614 A1 | 6/2000 |
| WO | WO-0143640 | 6/2001 |
| WO | WO-0158337 | 8/2001 |
| WO | WO-0166189 A1 | 9/2001 |
| WO | WO-0180709 A2 | 11/2001 |
| WO | WO-02058791 A1 | 8/2002 |
| WO | WO-03/013654 A1 | 2/2003 |
| WO | WO-03070105 | 8/2003 |
| WO | WO-03097162 A2 | 11/2003 |
| WO | WO-03098232 A2 | 11/2003 |
| WO | WO-2004093686 | 11/2004 |
| WO | WO-200558029 | 6/2005 |
| WO | WO-2005058029 A2 | 6/2005 |
| WO | WO-2006018837 A2 | 2/2006 |
| WO | WO-2006025001 A1 | 3/2006 |
| WO | WO-2006087649 A1 | 8/2006 |
| WO | WO-2006119572 | 11/2006 |
| WO | WO-2007073551 A1 | 6/2007 |
| WO | WO-2007093998 | 8/2007 |
| WO | WO-2008039449 | 4/2008 |
| WO | WO-2008050278 A1 | 5/2008 |
| WO | WO-200875203 | 6/2008 |
| WO | WO-2008075203 A2 | 6/2008 |
| WO | WO-2008119054 A1 | 10/2008 |
| WO | WO-2009055587 A1 | 4/2009 |
| WO | WO-2009094554 | 7/2009 |

OTHER PUBLICATIONS

Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).

Chen et al., "MR Acoustic Radiation Force Imaging: Comparison of Encoding Gradients.".

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).

Herbert et al., "Energy-based adaptive focusing of waves: application to ultrasonic transcranial therapy," 8th Intl. Symp. On Therapeutic Ultrasound.

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

International Preliminary Report on Patentability in International Patent Application No. PCT/IB2004/001512, mailed Dec. 8, 2005.

International Search Report and Written Opinion in International Patent Application No. PCT/IB2004/001498, dated Aug. 31, 2004.

(56) References Cited

OTHER PUBLICATIONS

International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.
International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. On Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatmene%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).
McGough, et al., "Direct Computation of Ultrasound Phased-Array Driving Signals from a Specified Temperature Distribution for Hyperthermia," IEEE Trans. On Biomedical Engineering, vol. 39, No. 8, pp. 825-835 (Aug. 1992).
McDannold, et al., "Quality Assurance and System Stability of a Clinical MRI-guided focused ultrasound system: Four-year experience," Medical Physics, vol. 33, No. 11, pp. 4307-4313 (Oct. 2006).
Soher et al., "Correcting for BO Field Drift in MR Temperature Mapping with Oil References," Proceedings of the Intl. Society for Magnetic Resonance in Medicine, (May 2008).
International Search Report and Written Opinion issued Dec. 2, 2010 for International Application No. PCT/IB2010/044345 (11 pages).

\* cited by examiner

ESTIMATION OF ALIGNMENT PARAMETERS IN MAGNETIC-RESONANCE-GUIDED ULTRASOUND FOCUSING

FIELD OF THE INVENTION

The present invention relates generally to ultrasound focusing and, more particularly, to calibrating magnetic-resonance-guided focused ultrasound systems.

BACKGROUND

Ultrasound penetrates well through soft tissues and, due to its short wavelengths, can be focused to spots with dimensions of a few millimeters. As a consequence of these properties, ultrasound can and has been used for a variety of diagnostic and therapeutic medical purposes, including ultrasound imaging and noninvasive surgery. For example, focused ultrasound may be used to ablate diseased (e.g., cancerous) tissue without causing significant damage to surrounding healthy tissue. The noninvasive nature of ultrasound surgery is particularly appealing for the treatment of, for example, brain tumors.

An ultrasound focusing system generally utilizes an acoustic transducer surface, or an array of transducer surfaces, to generate an ultrasound beam. In transducer arrays, the individual surfaces are typically individually controllable, i.e., their vibration phases and/or amplitudes can be set independently of one another, allowing the beam to be steered in a desired direction and focused at a desired distance. In medical applications, the target location of the ultrasound focus is often determined using magnetic resonance imaging (MRI). In brief, MRI involves placing a subject, such as the patient, into a static magnetic field, thus aligning the spins of hydrogen nuclei in the tissue, and then applying radio-frequency electromagnetic pulses to temporarily destroy the alignment, inducing a response signal. Different tissues produce different response signals, resulting in a contrast among theses tissues in MR images. Thus, MRI may be used to visualize, for example, a brain tumor, and determine its location relative to the patient's skull. An ultrasound transducer system, such as an array of transducers attached to a housing, may then be placed on the patient's head, and the transducers driven so as to focus ultrasound onto the tumor. This method is referred to as magnetic-resonance-guided focusing of ultrasound (MRgFUS).

In MRgFUS, the treatment target is defined in magnetic resonance (MR) coordinates. To enable directing the ultrasound focus onto this target, the location and orientation of the transducer(s) need to be ascertained in MR coordinates as well. The transducer coordinates may be measured directly in the MR coordinate system using MR trackers—e.g., fiducials visible in MR images—that are rigidly attached to the transducer system, or have an otherwise fixed and known relative location with respect to the transducer(s). MR trackers may be implemented in various ways, for example, as MRI markers or microcoils.

Ideally, the acoustic surface and the MR trackers would be perfectly placed and aligned with respect to each other. In practice, however, mechanical tolerances in production are inevitable, and the relative positions of the transducer(s) and the MR trackers generally deviate from the nominal relative positions due to these "production errors." As a result, if a transducer array is driven based on the nominal relative positions, the ultrasound focus will deviate from the intended focus. To ensure that the ultrasound focus more accurately coincides with the intended target, there is, accordingly, a need to quantify the effect of production errors on the accuracy of targeting.

SUMMARY

The present invention provides, in various embodiments, systems and methods for calibrating MR-guided focused ultrasound systems to enable estimating, and compensating for, misalignment parameters between MR trackers and ultrasound transducers of a phased array. Generally, the calibration involves driving the phased array at different sets of transducer phases and/or amplitudes (hereinafter referred to as sonication geometries) to address different targets, and measuring the targeting errors (i.e., the deviations of the ultrasound focus location from the expected location) for these different sonication geometries. The measurements may be performed on an acoustic phantom, which may be made of a gel. The combined information about the sonication geometries and associated targeting errors, along with information about the experimental setup, allows the production errors to be estimated. In subsequent MRgFUS, these estimates may serve to compute adjustments in the sonication geometry so as to focus the ultrasound at the intended target location. Thus, embodiments of the invention improve the accuracy MRgFUS. In some embodiments, the ultrasound focus will coincide with the target location within a tolerance of 1 mm.

In a first aspect, therefore, various embodiments of the invention provide a method for calibrating a MRgFUS system. The method includes providing a phased array of ultrasound transducers that has at least one associated MR tracker (e.g., a micro-coil or MRI marker) with a fixed position relative to the array, and establishing MR coordinates of the MR trackers. The MR trackers and the array may be part of a single rigid structure. The method further includes creating an ultrasound focus with the phased array for each of a plurality of sonication schemes, and establishing parameters indicative of MR coordinates of the ultrasound focus. These parameters may be, for example, the MR coordinates of the ultrasound focus, or coordinates of one or more projections of the ultrasound focus. The ultrasound focus may be created in a phantom, and the parameters may be established using any suitable MRI technique, for example, thermal MRI or acoustic-radiation-force MRI. Based at least in part on the parameters, a geometric relationship between the ultrasound transducers and the MR trackers is then determined. The determination of the geometric relationship may further be based on the sonication schemes.

In some embodiments, the geometric relationship includes coordinates of the MR trackers in a transducer coordinate system. Determining the geometric relationship may include determining a transformation between the MR coordinate system and the transducer coordinate system that is based, at least in part, on the parameters indicative of the MR coordinates of the ultrasound foci and on the sonication schemes, and using the transformation to determine the coordinates of the MR trackers in the transducer coordinate system.

In some embodiments, the geometric relationship includes production errors indicative of a deviation of the fixed relative positions between the MR trackers and the transducers from nominal relative positions. In this case, a transformation between the parameters and the production errors may be determined based, at least in part, on the sonication scheme. Further, a linear estimation method (e.g., a least square method) may be applied to the transformation and the ultrasound focus parameters to determine the production errors.

In a second aspect, a method for operating a magnetic-resonance-guided focused-ultrasound system is provided. Embodiments of the method include providing a phased array of ultrasound transducers with one or more associated MR trackers, and calibrating this system by establishing MR coordinates of the MR trackers, creating ultrasound foci for a plurality of sonication schemes and establishing parameters indicative of MR coordinates of the ultrasound foci, and determining a geometric relationship between the ultrasound transducers and the MR trackers based, at least in part, on the parameters. The method further includes operating the magnetic-resonance-guided focused-ultrasound system by focusing ultrasound into a target region with MR coordinates, based on the geometric relationship.

In a third aspect, a system for calibrating a magnetic-resonance-guided ultrasound-focusing system is provided. Embodiments of the system include a phased array of ultrasound transducers, an MRI apparatus, and a control facility. Associated with the ultrasound transducer array is at least one MR tracker, whose position is fixed relative to the array. The functionalities of the control facility include driving the phased array according to a sonication scheme to generate an ultrasound focus, receiving MR imaging data indicative of MR coordinates of the ultrasound focus and the MR trackers, and determining a geometric relationship between the ultrasound transducers and the MR trackers based (at least in part) on the MR imaging data. The system may further include (or operate on) a phantom in which the ultrasound focus is generated.

In a fourth aspect, various embodiments of the invention provide a magnetic-resonance-guided ultrasound-focusing system including a phased array of ultrasound transducers with associated MR trackers, an MR imaging apparatus, a user interface facilitating selection of a target region in MR coordinates, and a control facility. The functionalities of the control facility include driving the phased array according to a sonication scheme to generate an ultrasound focus, receiving MR imaging data indicative of MR coordinates of the ultrasound focus and the MR trackers, determining a geometric relationship between the ultrasound transducers and the MR trackers based (at least in part) on the MR imaging data, and operating the magnetic-resonance-guided focused-ultrasound system by focusing ultrasound into the target region based on the geometric relationship.

BRIEF DESCRIPTION OF THE DRAWINGS

The foregoing discussion and the following detailed description of embodiments of the invention can more readily be understood in conjunction with the accompanying drawings wherein.

DETAILED DESCRIPTION

Figure 1:
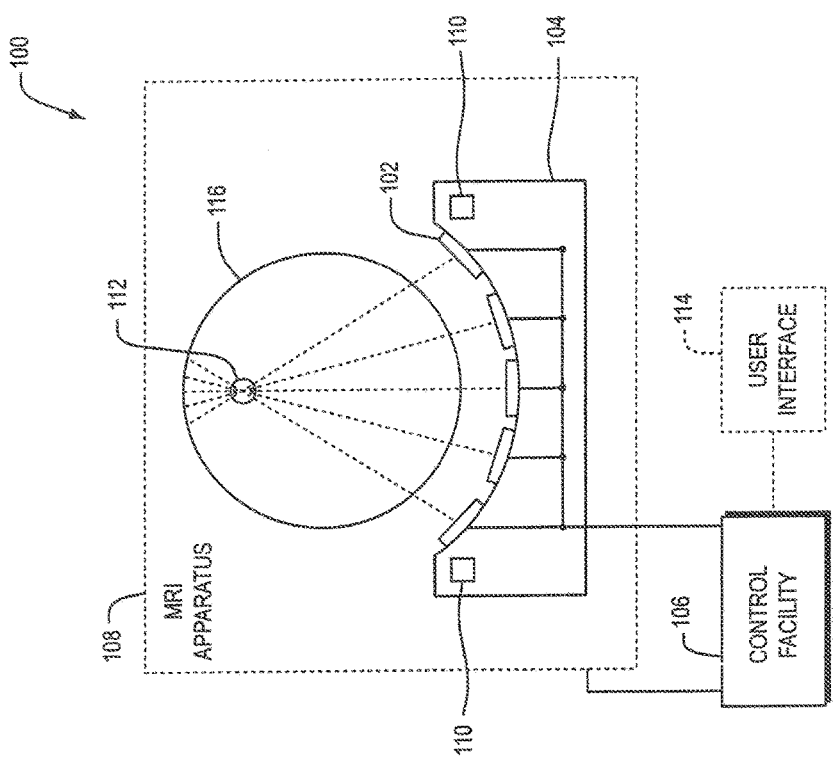
FIG. 1 is schematic diagram of an MRgFUS system in accordance with various embodiments.

The present invention is generally directed to the calibration of MRgFUS systems. An exemplary MRgFUS system 100 is illustrated schematically in FIG. 1. The system includes a plurality of ultrasound transducers 102, which are arranged in an array at the surface of a housing 104. The array may comprise a single row or a matrix of transducer elements 102. In alternative embodiments, the transducer elements 102 may be arranged in a non-coordinated fashion, i.e., they need not be spaced regularly or arranged in a regular pattern. The array may have a curved (e.g., spherical or parabolic) shape, as illustrated, or may include one or more planar or otherwise shaped sections. Its dimensions may vary, depending on the application, between millimeters and tens of centimeters. The transducer elements 102 may be piezoelectric ceramic elements. Piezo-composite materials, or generally any materials capable of converting electrical energy to acoustic energy, may also be used. To damp the mechanical coupling between the elements 102, they may be mounted on the housing using silicone rubber or any other suitable damping material.

The transducers 102 are separately controllable, i.e., they are each capable of emitting ultrasound waves at amplitudes and/or phases that are independent of the amplitudes and/or phases of the other transducers. A control facility 106 serves to drive the transducers 102. For n transducer elements, the control facility 106 may contain n control circuits each comprising an amplifier and a phase delay circuit, each control circuit driving one of the transducer elements. The control facility may split a radio frequency (RF) input signal, typically in the range from 0.1 MHz to 4 MHz, into n channels for the n control circuit. It may be configured to drive the individual transducer elements 102 of the array at the same frequency, but at different phases and different amplitudes so that they collectively produce a focused ultrasound beam. The control facility 106 desirably provides computational functionality, which may be implemented in software, hardware, firmware, hardwiring, or any combination thereof, to compute the required phases and amplitudes for a desired focus location. In general, the control facility may include several separable apparatus, such as a frequency generator, a beamformer containing the amplifier and phase delay circuitry, and a computer (e.g., a general-purpose computer) performing the computations and communicating the phases and amplitudes for the individual transducers 102 to the beamformer. Such systems are readily available or can be implemented without undue experimentation.

Figure 2:
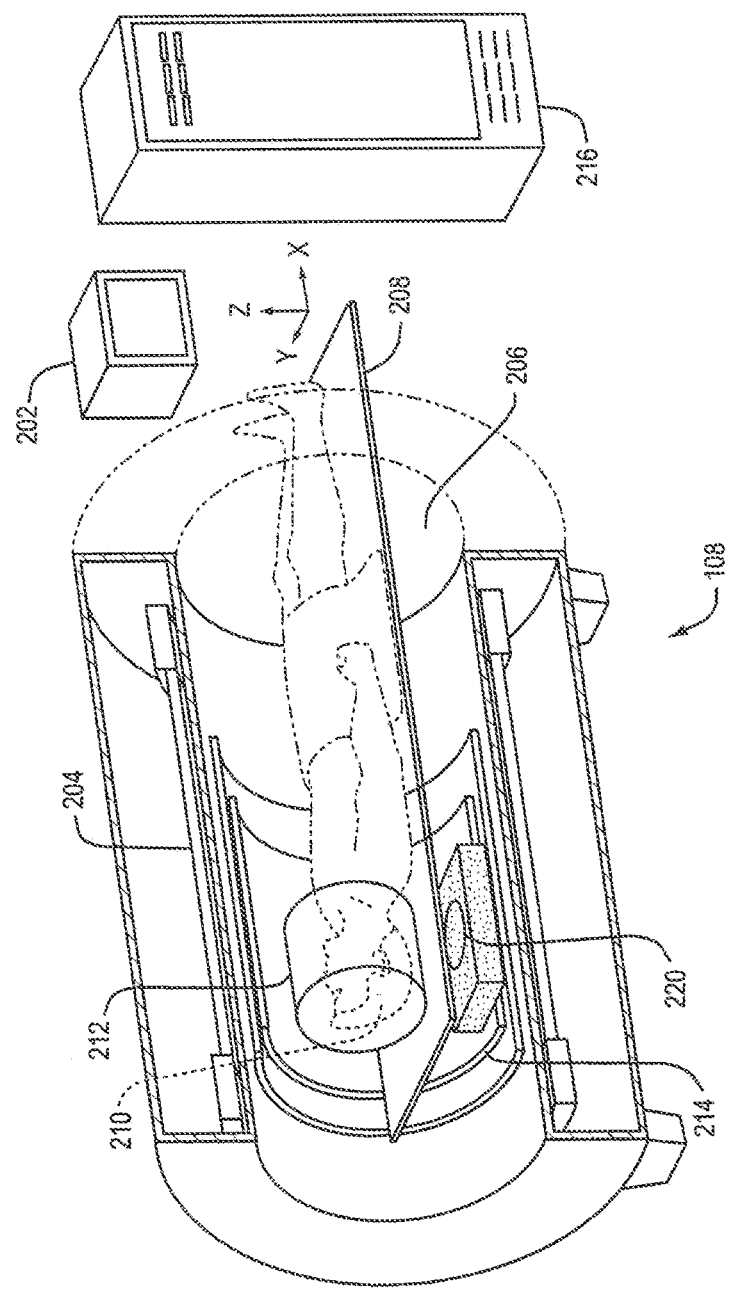
FIG. 2 shows an MRI machine suitable for MRgFUS applications in accordance with various embodiments.

The MRgFUS system 100 further includes an MRI apparatus 108 in communication with the control facility 106. An exemplary apparatus 108 is illustrated in more detail in FIG. 2. The apparatus 108 may include a cylindrical electromagnet 204, which generates a static magnetic field within a bore 206 of the electromagnet 204. During medical procedures, a patient is placed inside the bore 206 on a movable support table 208. A region of interest 210 within the patient (e.g., the patient's head) may be positioned within an imaging region 212 wherein the magnetic field is substantially homogeneous. A radio-frequency (RF) transmitter coil 214 surrounding the imaging region 212 emits RF pulses into the imaging region 212, and receives MR response signals emitted from the region of interest 210. The MR response signals are amplified, conditioned, and digitized into raw data using an image processing system 216, and further transformed into arrays of image data by methods known to those of ordinary skill in the art. Based on the image data, a treatment region (e.g., a tumor) is identified. An ultrasound phased array 220, disposed within the bore 206 of the MRI apparatus and, in some embodiments, within the imaging region 212, is then driven so as to focus ultrasound into the treatment region. This requires precise knowledge of the position and orientation of the transducer surface(s) with respect to the MRI apparatus.

Referring again to FIG. 1, the phased array of transducer 102 has MR trackers 110 associated with it. The MR trackers 110 may be incorporated into or attached to the housing 104, or otherwise arranged at a fixed position and orientation relative to the transducer array. Typically, three or more MR trackers 110 are used. If the relative positions and orientations of the MR trackers 110 and transducers 102 are known, MR scans of the MR trackers 110 implicitly reveal the transducer location in MRI coordinates, i.e., in the coordinate system of the MRI apparatus 108. The MR scan(s) may include image and/or spectral data. The control facility 106, which receives MRI data containing the MR tracker location, can then set the phases and amplitudes of the transducers 102 to generate a focus 112 at a desired location or within a desired target region. In some embodiments, a user interface 114 in communication with the control facility 106 and/or the MRI apparatus 108 facilitates the selection of the focus location or region in MR coordinates.

Typically, the relative positions of MR trackers 110 and transducers 102 are only approximately known. In order to obtain more accurate values for the relative positions, or their difference from the nominal, assumed values (i.e., the production errors), the system 100 may be calibrated. During calibration, the array of transducers 102 is attached to or located about an acoustic phantom 116, wherein an ultrasound focus may be generated.

Figure 3A:
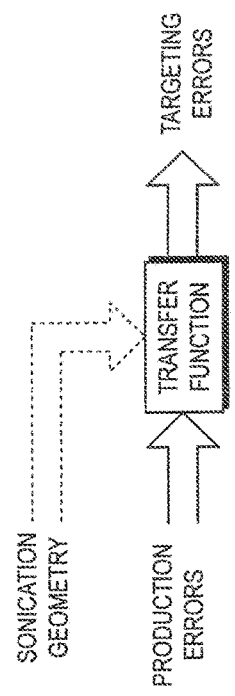
FIG. 3A is a schematic diagram illustrating the relationship between production errors and targeting errors in accordance with various embodiments.

The location of the ultrasound focus 112 in the phantom 116 depends on the particular sonication scheme as well as quantities characterizing the experimental setup, which may include, e.g., the speed of sound in the phantom, the incidence angle of ultrasound waves onto the surface of the phantom 116, and/or measurement distortions associated with the MRI apparatus 108. The relationship between the targeting errors and the production errors likewise depends on the sonication scheme and the setup quantities (i.e., nominal setup quantities and unknown setup errors). FIG. 3A illustrates this relationship, which may be expressed mathematically in terms of a transfer function. The transfer function takes the production errors and any setup errors as input variables and the sonication scheme and nominal setup quantities as parameters, and yields the targeting errors as output variables.

Although the production and setup errors are not known a priori, the transfer function itself is known from the nominal setup quantities and the selected sonication scheme. The transfer function may be given in the form of an algorithm for computing, for any hypothetical production error, the resulting targeting error. An exemplary such algorithm may involve (i) determining the position(s) and orientation(s) of the transducer surface(s) from their nominal relative positions to the trackers and the production errors; (ii) computing the location of the ultrasound focus based on the transducer location(s) and orientation(s) and the sonication scheme; (iii) determining "nominal" position(s) and orientation(s) of the transducer surface(s) from their nominal relative positions to the trackers alone, assuming that the production errors are zero; (iv) computing the location of the ultrasound focus based on the "nominal" transducer location(s) and orientation(s) and the sonication scheme; and (v) computing the difference between the two focus locations. Methods for computing the location of an ultrasound focus generated by a phased array of transducers driven according to a particular sonication scheme are described, for example, in U.S. patent application Ser. No. 12/425,698, filed Apr. 17, 2009, the entire contents of which are hereby incorporated herein by reference in their entirety.

Provided that the experimental setup does not change, the targeting errors are repeatable for each particular sonication scheme. By generating ultrasound foci in the phantom in accordance with a suitable set of different sonication schemes, and measuring the resulting targeting errors, production errors may be ascertained, or rendered "observable," as the term is used in estimation theory. Assuming that three-dimensional MR coordinates of the ultrasound focus can be determined for each sonication scheme, three sonications are needed to determine the position of the transducer in three dimensions. If only partial information can be derived from each sonication, however, the required number of sonication schemes is higher. An increased number of sonication schemes may also serve to improve statistics and reduce the effect of random errors. On the other hand, if constraints are placed on the positions of the transducers, or if not all of the positional information is desired (e.g., if the rotation of the transducer about itself is not relevant), fewer sonication schemes may suffice.

Accordingly, in various embodiments, the present invention facilitates determination of the relative positions between ultrasound transducers 102 and MR trackers 110 or, in other words, the relationship between ultrasound and MR coordinates. Methods in accordance with the invention involve, first, attaching the phased array of transducers 102 to the acoustic phantom 116, and introducing the arrangement into the MRI apparatus 108. Next, various sonication schemes are applied to the transducers 102, and the phantom and transducer setup is imaged using MRI techniques. Suitable imaging techniques include, for example, thermal imaging and acoustic radiation force imaging. Image acquisition may be three-dimensional or may, alternatively, provide a set of one- or two-dimensional images, which may be suitable for constructing a three-dimensional image. In the MR images, the focus location and/or targeting errors may be measured in terms of MR coordinates or related parameters. For example, the focal spot may be projected into a specific image plane, and the projection coordinates of the focus determined. The parameters indicative of the focus and/or targeting errors for the various sonication schemes may then be processed to estimate the relationship between the ultrasound and MR coordinates. This estimation step may be implemented in various ways.

Figure 3B:
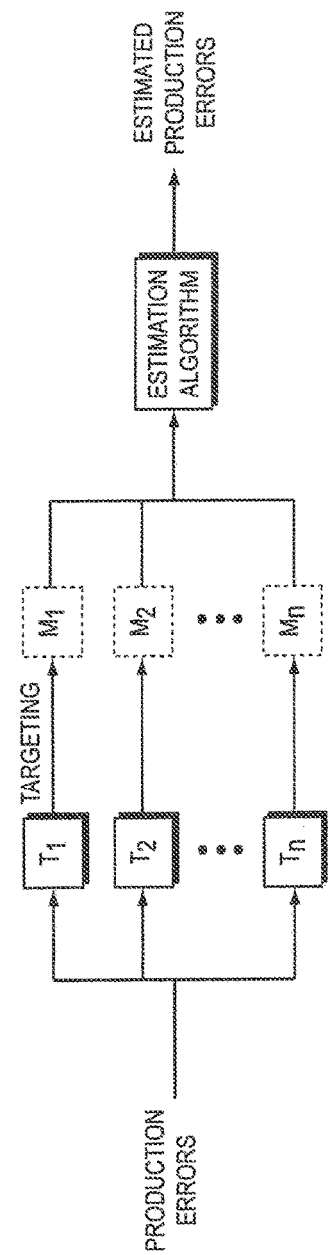
FIG. 3B is a schematic diagram illustrating a method for estimating production errors in accordance with one embodiment.

In one approach, the relationship between production (and setup) and targeting errors is modeled with a linear transfer function. Such linear approximations are appropriate when the input and output variables are small, which is usually the case for the production errors and resulting targeting errors. A linear transfer function can be expressed as a matrix. In FIG. 3B, the transfer function associated with a specific sonication scheme k is denoted as $T_k$. Further denoting the production errors and setup errors associated with a particular MRgFUS system as a vector PE, and denoting the targeting errors resulting from the production errors for sonication scheme k as $TE^{(k)}$, the relationship between these three quantities is described by: $TE^{(k)}=T_k*PE$. The targeting errors $TE^{(k)}$ may, in some embodiments, be measured directly as coordinate differences between the desired and the actual ultrasound focus in three dimensions. In general, however, measurements obtain indirect data indicative of the targeting errors, such as coordinates of the desired and actual ultrasound focus in several projection planes. Denoting the measured quantities as a vector $\text{Mes}^{(k)}$ and the transfer function that relates the targeting errors to the measured quantities as $M_k$, and further accounting for noise inherent in measurements, the measured quantities can be expressed as: $\text{Mes}^{(k)}=M_k*\text{TE}^{(k)}+\text{noise}$. Therefore, for a sonication scheme k, the actually measured quantities are related to the production errors by: $\text{Mes}^{(k)}=M_k*T_k*\text{PE}+\text{noise}$. Herein, $M_k$ and $T_k$ are transfer functions known a priori from the sonication scheme and experimental setup, $\text{Mes}^{(k)}$ is measured, and PE is to be determined.

The equations for the different sonication schemes (k) can all be combined into one linear system of equations, symbolically described in terms of a matrix equation: $\text{Mes}=\text{MT}*\text{PE}+\text{Noise}$, wherein Mes is a vector of vectors $\text{Mes}^{(k)}$, and MT is a block matrix comprising the individual blocks $M_k*T_k$. This system of linear equations may be solved using linear estimation methods, such as, e.g., least-square methods, minimum-variance, weighted-least-squares, maximum-likelihood, L1-regression, and/or best-linear-estimation methods. Utilizing a least-square method, for example, the pseudo-inverse matrix $\text{MT}^{\#}$ of the product of MT and its transpose may be computed according to $\text{MT}^{\#}=(\text{MT}^T*\text{MT})^{-1}$, and then the production errors may be estimated by multiplying the pseudo-inverse matrix to the vector of measurements: $\text{PE}_{estimated}=\text{MT}^{\#}*\text{MT}^T*\text{Mes}$.

An alternative approach involves determining a transformation between the MR coordinate system and the transducer coordinate system based on MR coordinates of ultrasound foci generated at certain locations with respect to the transducers and, therefore, at known transducer coordinates. Once this transformation is found, it can be applied to the MR tracker positions in the MR coordinate system to yield the MR tracker positions in the ultrasound coordinate system. This approach does not include determining target errors and, therefore, does not require initial estimates of MR tracker locations relative to the transducers.

The transformation between the transducer and the MR coordinate systems is defined by a geometric relationship therebetween. This relationship, in turn, can be determined from the transducer and MR coordinates of a sufficient number of suitably located ultrasound foci. In practice, however, it is not trivial to find the foci. Firstly, the ultrasound focus spot is usually elongated along the direction of the ultrasound beam. Secondly, a correct measurement of the focus location in the MR coordinate system requires an MR image that goes through the center of the ultrasound focus. In two-dimensional MR imaging, finding this center may require many scans, and constitute a cumbersome process. To overcome these difficulties, in one embodiment, the ultrasound focus locations are confined to two planes, as illustrated in FIG. 4.

Figure 4:
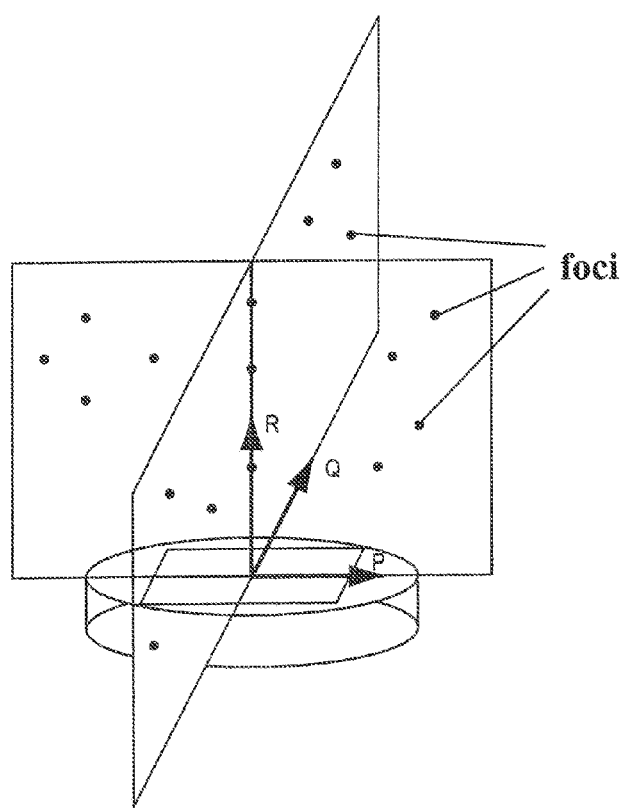
FIG. 4 is a schematic diagram illustrating ultrasound focus locations in two planes in accordance with one embodiment.

FIG. 4 schematically depicts a transducer surface (which may comprise a plurality of individual transducers), and defines a coordinate system associated with the transducer surface. The origin of the coordinate system lies in the transducer surface, and three mutually perpendicular axes P, Q, and R emanate from the origin. Axes P and Q are tangential to the surface at the origin, whereas R is normal to the surface. The transducer surface successively generates ultrasound foci either in a plane spanned by P and R, or in a plane spanned by Q and R. MRI scans are performed parallel to the plane spanned by P and Q. The scans need not go through the center of the focus; it suffices if they intersect the elongated focus spot because each apparent focus found in the scan plane is the intersection of the scan plane with a ray, in the PR or QR plane, from the origin of the transducer system to the actual focus, and thus lies in the same plane as the focus center.

To find the transformation between the MR and transducer coordinate systems, the MR coordinates of the measured (apparent) foci are sorted into those that belong to foci in the PR plane and those that belong to foci in the QR plane. From these data, a best fit to each of the two point collections defines the planes in the MR coordinate system. The intersection of the QR and PR planes defines the R direction. The R direction and the PR plane together then define the P direction, and, similarly, the R direction and the QR plane together define the Q direction. The only parameter that remains to be determined is the position of the origin along the R axis. This parameter can be determined from a best fit for an origin that would produce the measured focus positions, or from one or a few additional sonications.

Although the present invention has been described with reference to specific details, it is not intended that such details should be regarded as limitations upon the scope of the invention, except as and to the extent that they are included in the accompanying claims.

What is claimed is:

1. A method for calibrating a magnetic-resonance-guided focused-ultrasound system, comprising:
    (a) providing a phased array of ultrasound transducers, the array having at least one magnetic resonance (MR) tracker associated therewith at a fixed relative position with respect thereto;
    (b) establishing MR coordinates of the MR trackers;
    (c) for each of a plurality of sonication schemes, (i) creating an ultrasound focus, and (ii) establishing parameters indicative of MR coordinates of the ultrasound focus, wherein each sonication scheme is associated with a scheme-specific set of production errors; and,
    (d) based at least in part on the parameters, determining a geometric relationship between the ultrasound transducers and the MR trackers.

2. The method of claim 1 wherein the MR trackers and the array are part of a single rigid structure.

3. The method of claim 1 wherein the MR trackers comprise at least one of a micro-coil or an MR imaging marker.

4. The method of claim 1 wherein the ultrasound focus is created in a phantom.

5. The method of claim 1 wherein establishing the MR coordinates of the ultrasound focus comprises at least one of thermal MR imaging or acoustic-radiation-force MR imaging.

6. The method of claim 1 wherein the parameters comprise the MR coordinates of the ultrasound focus.

7. The method of claim 1 wherein the parameters comprise MR coordinates of a projection of the ultrasound focus.

8. The method of claim 1 wherein the determination of the geometric relationship is further based on the sonication schemes.

9. The method of claim 1 wherein the geometric relationship comprises coordinates of the MR trackers in a transducer coordinate system.

10. The method of claim 9 wherein determining the geometric relationship comprises determining a transformation between the MR coordinate system and the transducer coordinate system based, at least in part, on the parameters and the sonication schemes.

11. The method of claim 10 wherein determining the geometric relationship further comprises using the transformation to determine the coordinates of the MR trackers in the transducer coordinate system.

12. The method of claim 1 wherein the geometric relationship comprises production errors indicative of a deviation of the fixed relative positions between the MR trackers and the transducers from nominal relative positions.

13. The method of claim 12 wherein determining the geometric relationship comprises determining a transformation between the parameters and the production errors based, at least in part, on the sonication scheme.

14. The method of claim 13 wherein determining the geometric relationship further comprises applying a linear estimation method to the transformation and the parameters, thereby determining the production errors.

15. The method of claim 14 wherein the linear estimation method comprises a least square method.

16. A method for operating a magnetic-resonance-guided focused-ultrasound system, comprising:
 (a) providing a phased array of ultrasound transducers, the array having at least one magnetic resonance (MR) tracker associated therewith at a fixed relative position with respect thereto;
 (b) establishing MR coordinates of the MR trackers;
 (c) for each of a plurality of sonication schemes, (i) creating an ultrasound focus, and (ii) establishing parameters indicative of MR coordinates of the ultrasound focus, wherein each sonication scheme is associated with a scheme-specific set of production errors;
 (d) based at least in part on the parameters, determining a geometric relationship between the ultrasound transducers and the MR trackers; and
 (e) operating the magnetic-resonance-guided focused-ultrasound system by focusing ultrasound into a target region having MR coordinates, based on the geometric relationship.

17. A system for calibrating a magnetic-resonance-guided ultrasound-focusing system comprising:
 (a) a phased array of ultrasound transducers, the array having at least one magnetic resonance (MR) tracker associated therewith at a fixed relative position with respect thereto;
 (b) an MR imaging apparatus; and
 (c) a control facility for (i) driving the phased array according to a sonication scheme, associated with a scheme-specific set of production errors, so as to generate an ultrasound focus, (ii) receiving MR imaging data indicative of MR coordinates of the ultrasound focus and the MR trackers, and (iii) determining a geometric relationship between the ultrasound transducers and the MR trackers based, at least in part, on the MR imaging data.

18. The system of claim 17 further comprising a phantom in which the ultrasound focus is generated.

19. A magnetic-resonance-guided ultrasound-focusing system comprising:
 (a) a phased array of ultrasound transducers, the array having at least one magnetic resonance (MR) tracker associated therewith at a fixed relative position with respect thereto;
 (b) an MR imaging apparatus;
 (c) a user interface facilitating selection of a target region in MR coordinates; and
 (d) a control facility for (i) driving the phased array according to a sonication scheme, associated with a scheme-specific set of production errors, so as to generate an ultrasound focus, (ii) receiving MR imaging data indicative of MR coordinates of the ultrasound focus and the MR trackers, (iii) determining a geometric relationship between the ultrasound transducers and the MR trackers based, at least in part, on the MR imaging data, and (iv) operating the magnetic-resonance-guided focused-ultrasound system by focusing ultrasound into the target region based on the geometric relationship.

* * * * *